United States Patent
Grossmann et al.

(10) Patent No.: US 9,284,064 B2
(45) Date of Patent: Mar. 15, 2016

(54) LINING/FAIRING PANEL AND METHOD FOR MEASURING THE ELECTRICAL BONDING RESISTANCE OF A LINING/FAIRING PANEL

(71) Applicant: Airbus Operations GmbH, Hamburg (DE)

(72) Inventors: Matthias Grossmann, Norderstedt (DE); Michael Kaste, York (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 426 days.

(21) Appl. No.: 14/066,772

(22) Filed: Oct. 30, 2013

(65) Prior Publication Data

US 2014/0132289 A1 May 15, 2014

Related U.S. Application Data

(60) Provisional application No. 61/725,054, filed on Nov. 12, 2012.

(30) Foreign Application Priority Data

Nov. 12, 2012 (EP) .................................... 12192226

(51) Int. Cl.
*G01R 27/02* (2006.01)
*B64D 45/02* (2006.01)
*B64F 5/00* (2006.01)

(52) U.S. Cl.
CPC .............. *B64D 45/02* (2013.01); *B64F 5/0045* (2013.01); *G01R 27/02* (2013.01)

(58) Field of Classification Search
CPC ....................................................... B64D 45/02
USPC .................. 324/525, 691, 541, 544, 551, 557
See application file for complete search history.

(56) References Cited

U.S. PATENT DOCUMENTS

| 4,755,904 | A | 7/1988 | Brick | |
|---|---|---|---|---|
| 7,633,283 | B2 * | 12/2009 | Georgeson et al. | 324/72 |
| 8,264,215 | B1 | 9/2012 | Kovach et al. | |

(Continued)

FOREIGN PATENT DOCUMENTS

| DE | 3514150 C1 * | 4/1986 |
|---|---|---|
| EP | 1484245 A1 | 8/2004 |
| EP | 1887366 A2 | 2/2008 |

(Continued)

OTHER PUBLICATIONS

European Searching Authority, European Search Report for 12192226 Mailed Apr. 3, 2013.

*Primary Examiner* — Vincent Q Nguyen
(74) *Attorney, Agent, or Firm* — Ingrassia Fisher & Lorenz, P.C.

(57) ABSTRACT

A lining/fairing panel, in particular a lining/fairing panel for an airborne vehicle such as an aircraft or a spacecraft is provided. The lining/fairing panel includes a panel body having a first surface and a second surface opposite to the first surface, an electrically conductive coating applied to the first surface or the second surface, and a via arranged in the panel body reaching from the first surface to the second surface of the panel body. The via is formed in an inner region of the panel body. The borders of the inner region are spaced apart by a predetermined distance from the borders of the first and second surface of the panel body.

8 Claims, 2 Drawing Sheets

(56) References Cited

U.S. PATENT DOCUMENTS

2011/0014356 A1\* 1/2011 Fornes et al. .................. 427/58
2011/0247203 A1 10/2011 Lopez-Reina Torrijos

FOREIGN PATENT DOCUMENTS

| EP | 2402248 | A2 | | 1/2012 |
| GB | 2255314 | A | \* | 11/1992 |

\* cited by examiner

LINING/FAIRING PANEL AND METHOD FOR MEASURING THE ELECTRICAL BONDING RESISTANCE OF A LINING/FAIRING PANEL

CROSS-REFERENCES TO RELATED APPLICATIONS

This application claims priority to U.S. Provisional Patent Application No. 61/725,054, filed Nov. 12, 2012, and to European Patent Application No. 12 192 226.4, filed Nov. 12, 2012, which are each incorporated herein by reference in their entirety.

TECHNICAL FIELD

This application pertains to a lining/fairing panel and a method for measuring the electrical bonding resistance of a lining/fairing panel, particularly to be used for an electromagnetic and lightning protection lining/fairing of an aircraft or spacecraft.

BACKGROUND

Non-conductive panels for an airborne vehicle such as an aircraft or a spacecraft represent an electromagnetic aperture in the internal and external hull of the airborne vehicle. In order to protect an aircraft from the effects of lightning strikes and High Intensity External Radiated Fields (HIRF), a conductive layer is usually applied to the surface of such lining and fairing panels. The conductive layer is electrically connected to adjacent conductive structural components of the airborne vehicle such as metallic fuselage or hull parts.

In order to check the proper functionality of the lining/fairing panels after installation, it is desirable to measure the electrical bonding resistance between a lining/fairing panel with a conductive surface coating and the respective conductive structural components of the airborne vehicle to which the lining/fairing panel is attached. The electrical bonding resistance is an important parameter to ensure electromagnetic compatibility (EMC) and lightning protection capability of the lining/fairing of an airborne vehicle.

U.S. Pat. No. 4,755,904 A discloses a composite material skin attached to a composite material structure using metal lock bolts. A foraminous metal layer is arranged on the composite material skin to divert current generated by lightning strikes away from the metal lock bolts.

European Patent No. 2 402 248 A2 discloses aircraft panels made of composite materials having a metallization structure thereon and metal fixing elements stuck through bores in the aircraft panels for bonding the aircraft panels to structural aircraft elements.

In addition, other objects, desirable features and characteristics will become apparent from the subsequent summary and detailed description, and the appended claims, taken in conjunction with the accompanying drawings and this background.

SUMMARY

According to various embodiments, provided is a means to measure the electrical bonding resistance for a lining/fairing panel of an airborne vehicle to the structural elements of the airborne vehicle of which may be measured in readily accessible and uncomplicated manner.

According to a one of various aspects of the present disclosure, a lining/fairing panel, in particular a lining/fairing panel for an airborne vehicle such as an aircraft or a spacecraft, comprises a panel body having a first surface and a second surface opposite to the first surface, an electrically conductive coating applied to the first surface or the second surface, and a via arranged in the panel body reaching from the first surface to the second surface of the panel body, the via being formed in an inner region of the panel body the borders of which inner region are spaced apart by a predetermined distance from the borders of the first and second surface of the panel body.

According to another of various aspects of the present disclosure, an airborne vehicle comprises a plurality of lining/fairing panels according to various embodiments mounted on structural elements of the airborne vehicle.

According to one of various aspects of the present disclosure, a method for measuring the electrical bonding resistance of a lining/fairing panel according to various embodiments to a structural element of an airborne vehicle such as an aircraft or a spacecraft comprises forcing an electrical current through the bolt, the electrically conductive coating and the structural element, measuring a voltage drop between the bolt and the structural element, and determining the electrical bonding resistance of a lining/fairing panel dependent on the measured voltage drop.

One main idea of the present disclosure is to provide for a lining/fairing panel for use in an airborne vehicle which is part of an electromagnetic interference (EMI) and lightning protection system. The necessary electrically conductive bonding to the structural elements of the airborne vehicle on which the lining/fairing panel is mounted may be measured with the aid of an electrically conductive bolt arranged in a via reaching through the panel body of the lining/fairing panel. The bolt is electrically coupled to an electrically conductive coating applied to a surface of the panel body.

One advantage of such a lining/fairing panel is the ease of accessibility for measuring the electrical bonding resistance to the underlying structural element such as a fuselage or hull component. Irrespective of whether the electrically conductive coating faces the structural element, the bolt is always accessible from the outside, for example for resistance measurements.

Particularly advantageous is the fact that the electrically conductive coating will not have to be damaged or altered when measuring the electrical bonding resistance. This facilitates a measurement when the lining/fairing panel has already been applied in its final mounting place.

Finally, the electrical bonding resistance measurements may be performed easily in the component production phase, for example during acceptance test procedures, in the aircraft manufacturing phase after the installation of the lining/fairing panels, in a maintenance, repair and overhaul (MRO) phase or in a troubleshooting phase. This is particularly useful since the lining/fairing panels do neither need to be de-installed nor damaged for these kind of measurements.

The lining/fairing panel is thus always electrically accessible from both sides of the panel body.

According to an exemplary embodiment of the lining/fairing panel, the lining/fairing panel may comprise a bolt comprising an electrically conductive material arranged in the via, the bolt being electrically coupled to the electrically conductive coating.

According to another exemplary embodiment of the lining/fairing panel, the lining/fairing panel may further comprise a nut arranged on the second surface of the panel body, wherein the bolt is a threaded bolt threadingly engaging the nut.

According to one exemplary embodiment of the lining/fairing panel, the lining/fairing panel may further comprise a first washer comprising an electrically conductive material, the first washer being arranged between the nut and the second surface of the panel body.

According to another exemplary embodiment of the lining/fairing panel, the electrically conductive coating may be applied to the second surface of the panel body, and the first washer may extend over at least part of the electrically conductive coating electrically coupling the electrically conductive coating to the bolt.

According to one embodiment of the lining/fairing panel, the lining/fairing panel may further comprise a second washer comprising an electrically conductive material, the second washer being arranged between the bolt head and the first surface of the panel body.

According to another exemplary embodiment of the lining/fairing panel, the electrically conductive coating may be applied to the first surface of the panel body, and the second washer may extend over at least part of the electrically conductive coating electrically coupling the electrically conductive coating to the bolt.

According to one embodiment of the lining/fairing panel, the second washer may have a conical shape, and the via may comprise a conically shaped opening broadening towards the first surface configured to receive the second washer within the opening.

According to an exemplary embodiment of the lining/fairing panel, the panel body may comprise a monolithic and electrically non-conductive glass fibre composite material.

According to various embodiments of the lining/fairing panel, the panel body may comprise at least two layers of glass fibre composite material sandwiching a honeycomb core structure.

According to one exemplary embodiment of the lining/fairing panel, a filler of conductive or non-conductive material may be arranged in the sandwich panel body surrounding the via.

According to another embodiment of the lining/fairing panel, the lining/fairing panel may further comprise a surface protection layer applied to the electrically conductive coating.

A person skilled in the art can gather other characteristics and advantages of the disclosure from the following description of exemplary embodiments that refers to the attached drawings, wherein the described exemplary embodiments should not be interpreted in a restrictive sense.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the present disclosure or the application and uses of the present disclosure. Furthermore, there is no intention to be bound by any theory presented in the preceding background or the following detailed description.

Figure 1:
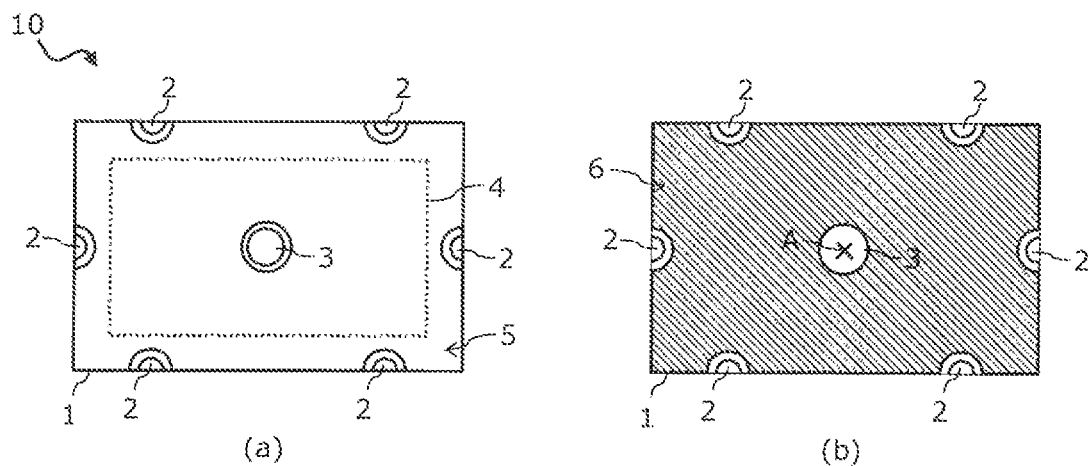
FIG. 1 shows a lining/fairing panel for an airborne vehicle according to various embodiments of the present disclosure.
Figure 7:
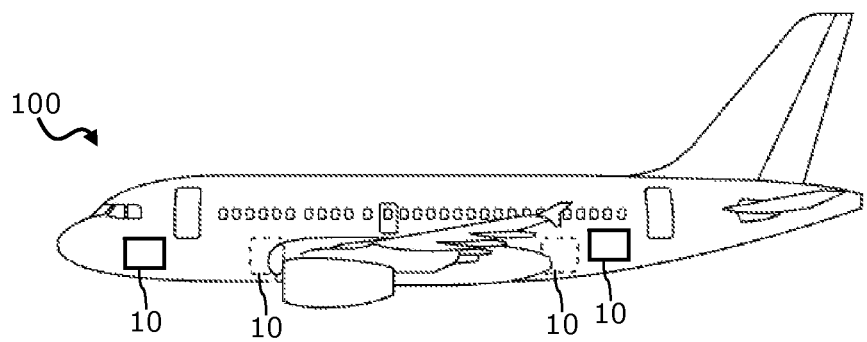
FIG. 7 shows an airborne vehicle having two lining/fairing panels according to various embodiments.

FIG. 1 shows a lining/fairing panel 10, particularly a lining/fairing panel 10 for use in an airborne vehicle such as an aircraft or spacecraft. One or more lining/fairing panels 10 may be used in an aircraft such as the aircraft 100 as shown exemplarily in FIG. 7. The aircraft 100 of FIG. 7 may comprise one or more lining/fairing panels 10 mounted to structural elements of the aircraft 100 such as fuselage or hull components. FIG. 1 shows two views of a lining/fairing panel 10—(a) is a view on one surface of the lining/fairing panel 10, whereas (b) is a view from the other side of the lining/fairing panel 10.

The lining/fairing panel 10 may comprise a panel body 1 which may be substantially oblong or rectangular in shape. Of course, other geometrical shapes and dimension of the lining/fairing panel body 1 may be possible as well. The lining/fairing panel 10 may substantially be flat or slightly curved depending on the area of the hull of an airborne vehicle where the lining/fairing panel 10 is intended to be mounted.

The panel body 1 may have a lower surface 5 and an upper surface opposite to the lower surface 5. The upper surface—in the case of FIG. 1 the top side of (b)—may be coated with an electrically conductive coating. The panel body 1 may comprise a generally electrically non-conductive material, for example glass fibre composite material or layered glass fibre composite material having a honeycomb core sandwiched between. Alternatively, the panel body 1 may comprise a carbon fibre resin plastic (CFRP) material.

The electrically conductive coating 6 may be applied to all or only part of the upper surface of the panel body and may for example comprise metal meshes, metal foils, sprayed metal, woven wire fabrics, metallized fiberglass, antistatic coatings, metal loaded paints or vapour deposited metal layers, made from, for example, copper, bronze, aluminium, nickel or silver. It may also be possible to use polyurethane or epoxy matrices having metallic nanoparticles made from silver, nickel, aluminium, bronze or copper dispersed therein. The electrically conductive coating 6 may additionally be coated with a surface protection layer (not shown), for example enamel, varnish or paint.

The panel body 1 may be fastened to the structural elements of an airborne vehicle by means of fasteners 2 arranged at the borders of the panel body 1. The number and type of fasteners may be chosen according to the needs of the area of application, bearing in mind to avoid corrosion of the fasteners and the electrically conductive coating 6 as much as possible. The panel body 1 may have an inner region 4 which is spaced apart from the borders of the panel body 1 by a predetermined distance. Within the inner region 4 one or more vias 3 may be arranged reaching the lower surface 5 to the upper surface and through the electrically conductive coating 6.

The via 3 may for example be a round through-hole, although other shapes may be possible for the via 3 as well. The via 3 may comprise a via axis A substantially oriented in parallel to a normal vector of the plane defined by the panel body 1.

As will be shown with respect to FIGS. 2 to 5, the via 3 is configured to receive a bolt 11 within the opening defined by the via 3.

Figure 2:
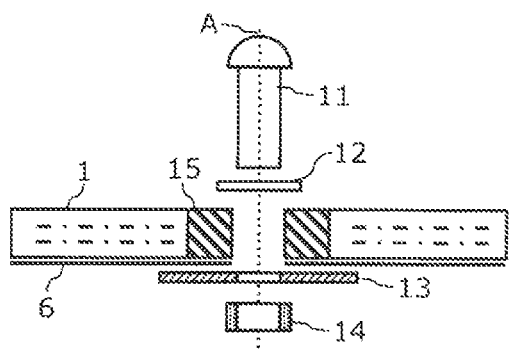
FIG. 2 shows a lining/fairing panel in greater detail according to another one of various embodiments of the present disclosure.
Figure 3:
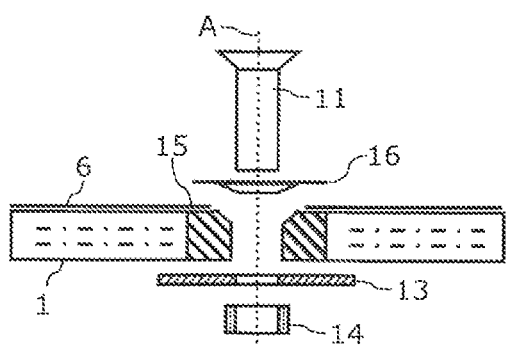
FIG. 3 shows a lining/fairing panel in greater detail according to another exemplary embodiment of the present disclosure.
Figure 4:
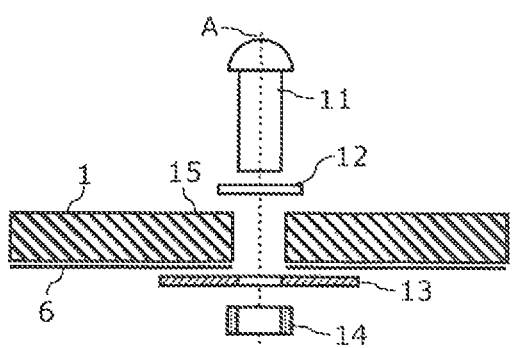
FIG. 4 shows a lining/fairing panel in greater detail according to another exemplary embodiment of the present disclosure.
Figure 5:
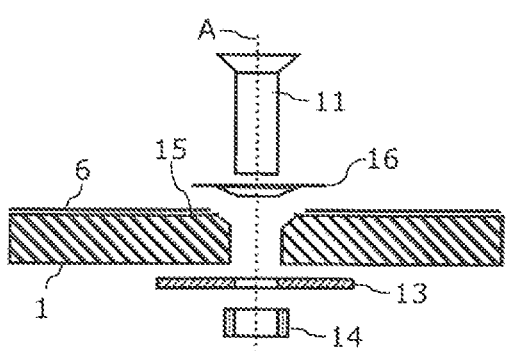
FIG. 5 shows a lining/fairing panel in greater detail according to another exemplary embodiment of the present disclosure.

FIGS. 3 and 5 refer to the situation where the electrically conductive coating 6 is applied on one of the surfaces of the panel body 1, in particular the surface adjacent to the bolt head of the bolt 11. On the contrary, FIGS. 2 and 4 refer to the situation where the electrically conductive coating 6 is applied on the opposite surface opposite to the bolt head of the bolt 11.

In FIGS. 4 and 5, the panel body 1 comprises a monolithic and electrically non-conductive glass fibre composite material. In FIGS. 2 and 3, the panel body 1 comprises a layered glass fibre composite material sandwiching a honeycomb core. For the FIGS. 2 and 3, in the surrounding of the via 3, filler material 15 may be arranged to mechanically stabilize the via 3.

Referring to the common features of FIGS. 2 to 5, a bolt 11 is arranged within the opening defined by the via 3. The bolt 11 may be a threaded bolt 11, which threadingly engages a nut 14 on the opposite side of the panel body 1. The bolt 11 may comprise an electrically conductive material such as aluminium, titanium, titanium alloy or stainless steel. The material of the bolt 11 may be chosen optimized for anti-corrosion properties.

Between the nut and the lower surface of the panel body 1, a first washer 13 may be arranged. The first washer 13 may be a flat washer. Between the bolt head of the bolt 11 and the upper surface of the panel body 1 a corresponding second washer 12 or 16 may be arranged. Depending on which surface of the panel body 1 the electrically conductive coating 6 is applied, the respective washer 12, 13 or 16 may have a washer rim extending over at least part of the electrically conductive coating 6 to electrically couple the coating 6 to the bolt 11.

In FIGS. 3 and 5, the second washer 16 may have a conical shape and the via 3 may define an opening having a conical shape widening towards the upper surface, the opening being configured to receive the second washer 16 therein. To that end, the edges of the filler material 15 may be slanted, bevelled or tapered correspondingly. The bolt 11 may in these cases be a counter sunk bolt or a counter sunk screw.

In FIGS. 2 and 4, the bolt 11 may in particular be a bolt having a rounded head such as a fillister head screw or a button head screw. In these cases the second washer 12 may be a flat washer frictionally engaged to the flat surface of the panel body 1.

Of course, the bolt and washer solution of FIGS. 2 and 4 may as well be employed in the embodiments of FIGS. 3 and 5 where the electrically conductive coating 6 is arranged on the opposite side. Similarly, the bolt and washer solution of FIGS. 3 and 5 may be employed in the embodiments of FIGS. 2 and 4.

The lining/fairing panel 10 as shown in FIGS. 1 to 5 may be mounted on or in an aircraft with the electrically conductive coating 6 facing the structural elements of the aircraft or with the electrically conductive coating 6 facing outside. Irrespective of what installation geometry is chosen, the bolt 11 is always accessible from outside to perform electrical bonding resistance measurements at the lining/fairing panel 10.

Figure 6:
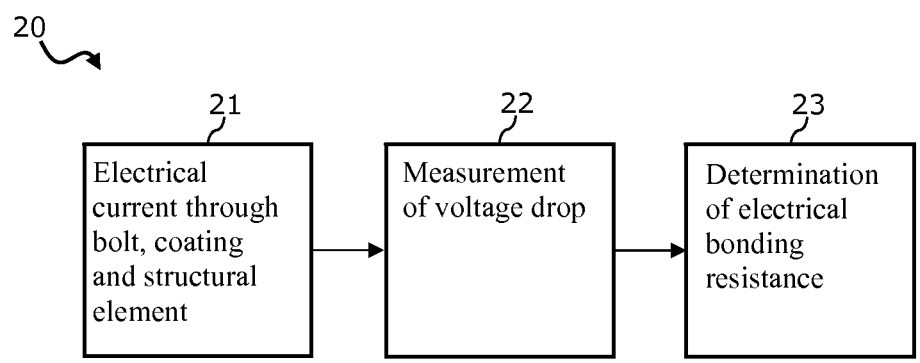
FIG. 6 shows a method for measuring the electrical bonding resistance of a lining/fairing panel according to various embodiments.

FIG. 6 schematically illustrates a method 20 for measuring the electrical bonding resistance of a lining/fairing panel such as the lining/fairing panel 10 as exemplarily explained in conjunction with FIGS. 1 to 5 to a structural element of an airborne vehicle. The method 20 may for example be employed for measurements of lining/fairing panels 10 installed on or in an aircraft such as the aircraft as exemplarily shown in FIG. 7. The method 20 may for example be used in the component production phase, for example during acceptance test procedures, in the aircraft manufacturing phase after the installation of the lining/fairing panels, in a maintenance, repair and overhaul (MRO) phase or in a troubleshooting phase.

At 21, an electrical current is forced through the bolt, the electrically conductive coating and the structural element. Then, at 22, a voltage drop between the bolt and the structural element is measured. Dependent on the measured voltage drop, the electrical bonding resistance of the lining/fairing panel 10 may be determined at 23. The method 20 may for example be implemented using a four point probe method or a two point probe method, wherein the resistance of the electrically conductive coating is dependent on a current flowing throughout the coating and a voltage drop between the coating and the structural element to which the lining/fairing panel is mounted.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the present disclosure as set forth in the appended claims and their legal equivalents.

What is claimed is:

1. A lining/fairing panel, comprising:
   a panel body having a first surface and a second surface opposite the first surface;
   an electrically conductive coating applied to the second surface;
   a via arranged in the panel body that extends from the first surface to the second surface of the panel body, the via being formed in an inner region of the panel body and a border of the inner region is spaced apart by a predetermined distance from a border of the first surface and a border of the second surface of the panel body;
   a bolt comprising an electrically conductive material arranged in the via, the bolt being electrically coupled to the electrically conductive coating;
   a nut arranged on the second surface of the panel body, wherein the bolt is a threaded bolt threadingly engaging the nut; and
   a first washer comprising an electrically conductive material, the first washer being arranged between the nut and the second surface of the panel body;
   wherein the first washer extends over at least part of the electrically conductive coating electrically coupling the electrically conductive coating to the bolt.

2. The panel of claim 1, further comprising:
   a second washer comprising an electrically conductive material, the second washer being arranged between a head of the bolt and the first surface of the panel body.

3. The panel of claim 1, wherein the panel body comprises a monolithic and electrically non-conductive glass fibre composite material.

4. The panel of claim 1, wherein the panel body comprises at least two layers of glass fibre composite material sandwiching a honeycomb core structure.

5. The panel of claim 4, wherein a filler of conductive or non-conductive material is arranged in the panel body surrounding the via.

6. The panel of claim 1, further comprising:
a surface protection layer applied to the electrically conductive coating.

7. An airborne vehicle, comprising:
one or more structural elements;
a plurality of lining/fairing panels mounted on the structural elements, each one of the plurality of panels including:
   a panel body having a first surface and a second surface opposite the first surface;
   an electrically conductive coating applied to the second surface;
   a via arranged in the panel body that extends from the first surface to the second surface of the panel body, the via being formed in an inner region of the panel body and a border of the inner region is spaced apart by a predetermined distance from a border of the first surface and a border of the second surface of the panel body;
   a bolt comprising an electrically conductive material arranged in the via, the bolt being electrically coupled to the electrically conductive coating;
   a nut arranged on the second surface of the panel body, wherein the bolt is a threaded bolt threadingly engaging the nut; and
   a first washer comprising an electrically conductive material, the first washer being arranged between the nut and the second surface of the panel body;
   wherein the first washer extends over at least part of the electrically conductive coating electrically coupling the electrically conductive coating to the bolt.

8. The airborne vehicle of claim 7, further comprising:
a second washer comprising an electrically conductive material, the second washer being arranged between a head of the bolt and the first surface of the panel body.

* * * * *